(12) United States Patent
Giansanti

(10) Patent No.: US 6,266,824 B1
(45) Date of Patent: Jul. 31, 2001

(54) HEAD SHIELD

(76) Inventor: Carlo Giansanti, 30 Lorraine Ter., Boonton, NJ (US) 07005

( * ) Notice: Subject to any disclaimer, the term of this patent is extended or adjusted under 35 U.S.C. 154(b) by 0 days.

(21) Appl. No.: 09/616,058

(22) Filed: Jul. 13, 2000

(51) Int. Cl.⁷ .................................................. A42B 1/00
(52) U.S. Cl. ............................ 2/200.1; 2/7; 2/171; 2/172; 2/195.1; 2/410
(58) Field of Search ............................ 2/6.6, 455, 7, 171, 2/172, 200.1, 410, 195.1, 8, 175.1, 411, 412; 250/515.1, 516.1; 607/1; 245/4, 6

(56) References Cited

U.S. PATENT DOCUMENTS

| | | | |
|---|---|---|---|
| 2,218,560 | * 10/1940 | Stephens | 245/6 |
| 3,164,840 | * 1/1965 | Reynolds | 2/2 |
| 4,980,564 | * 12/1990 | Steelmon | 250/505.1 |
| 5,073,984 | * 12/1991 | Tone et al. | 2/2 |
| 5,103,504 | * 4/1992 | Dordevic | 2/243 |
| 5,115,140 | * 5/1992 | Rodriguez | 250/516.1 |
| 5,511,241 | * 4/1996 | Ziegler | 2/2.5 |
| 5,570,476 | * 11/1996 | Olive | 2/200.1 |
| 5,621,188 | * 4/1997 | Lee et al. | 174/35 MS |
| 5,950,237 | * 9/1999 | Micheron et al. | 2/69 |
| 6,029,278 | * 2/2000 | Lopez | 2/209.13 |

\* cited by examiner

*Primary Examiner*—John J. Calvert
*Assistant Examiner*—Katherine Moran
(74) *Attorney, Agent, or Firm*—Peter A. Borsari

(57) ABSTRACT

An electromagnetic shielding apparatus for covering and protecting the head of a user from EMF radiation which may be worn by itself or discretely beneath other head gear. A head covering is fabricated from a conductive, non-magnetizable material such as copper, bronze, brass or the like which may be drawn and shaped into a web or mesh material. The resulting shield is lightweight, air permeable and supple enough to be worn beneath other head gear.

15 Claims, 1 Drawing Sheet

HEAD SHIELD

FIELD OF INVENTION

The invention relates to electromagnetic shielding for the head and particularly to a head shield which may be worn alone or in conjunction with other head gear. Specifically, the invention relates to a head shield fabricated from a light-weight metal mesh or web material having openings to permit air permeability.

BACKGROUND OF THE INVENTION

Living tissues of plants and animals depend on electrochemical potentials for many of their normal functions. Charged species such as sodium, potassium and calcium ions are nearly omnipresent throughout mammalian bodies and participate in or facilitate numerous important chemical reactions. Disruption of or interference with these reactions may occur due to chemical imbalances caused by environmental factors including the presence of electromagnetic radiation (EMR) sources, such as power lines, electrical equipment and the like. Recently, EMR sources have been implicated in the development of brain tumors, cancer, headaches, malaise, short-term memory loss and childhood leukemia. Both static electric and magnetic fields (collectively, EMF) as well as radiofrequency (RF) radiation have been implicated in these conditions and diseases. Unfortunately, with modern society's increasing reliance on electrical devices such as refrigerators, alarm clocks, microwave ovens, cellular phones, computers and the like, exposure to EMFs has become more consistent and unavoidable.

Notwithstanding efforts by numerous western nations and Japan to regulate exposure by their people to EMFs as well as regulatory efforts adopted by several states in the U.S., there is disagreement as to the significance of the role EMFs play in the development of disease, notably cancer, in humans. A peer-reviewed report appearing in the British journal *The Lancet* in December 1999 concluded that there was no link between electromagnetic radiation and childhood cancer in clear conflict with a report by James Clark and David Derbyshire in the Jul. 16, 1998 edition of the Daily Mail that indicated studies conducted by British researches found the use of mobile phones could "disrupt parts of the brain in charge of memory and learning" and could "cause a rise in blood pressure and may harm pregnant women." What is not in dispute is that humans in developed nations are exposed to EMFs as part of the modern environment and that the range of effects due to such exposure is not fully understood. Arguably, reduction or elimination of such exposure in the absence of clear understanding is to be desired. To this end, several attempts have been made in the prior art to reduce exposure by humans to various radiation sources. For example, U.S. Pat. No. 5,570,476, issued Nov. 5, 1996 to B. B. Olive discloses a cap of metallized fabric to protect the wearer from an electromagnetic field. U.S. Pat. No. 5,621,188, issued Apr. 15, 1997 to S. C. Lee et al. discloses an electromagnetic shielding medium which can be used on the head. The shielding medium can be composed of any highly conductive metal, such as copper, and is fabricated as a plurality of geometrically shaped objects (spheres) held in contact with each other in a generally hexagonal array. U.S. Pat. No. 5,038,047 issued Aug. 6, 1991 to S. S. Still discloses a hood to protect the head from radiation exposure. U.S. Pat. No. 5,022,099, issued Jun. 11, 1991 to C. A. Walton shows a solid helmet to protect the head from radiation.

Despite the efforts of the prior art, each of these devices fails to provide EMF shielding which is not only effective at shielding the head but also which is lightweight, thus making economical use of material, simple to manufacture, air permeable and supple enough to be worn comfortably under other head gear such as caps, hats or scarves.

SUMMARY OF THE INVENTION

Accordingly, it is an object of the present invention to provide an electromagnetic shielding apparatus that protects the head of a wearer from EMFs and which may be worn comfortably beneath or in conjunction with other head gear.

A further object of the invention is to provide an electromagnetic shielding apparatus which is lightweight and airpermeable.

A still further object of the invention is to provide an electromagnetic shielding apparatus which is simple to manufacture and makes economical use of material.

Additional objects, advantages and novel features of the invention will be set forth in part of the description which follows, and in part will become apparent to those skilled in the art upon examination of the following specification or may be learned by practice of the invention.

BRIEF DESCRIPTION OF THE DRAWINGS

The present invention will be better understood with reference to the appended drawing sheets, wherein.

DETAILED DESCRIPTION

Figure 1:
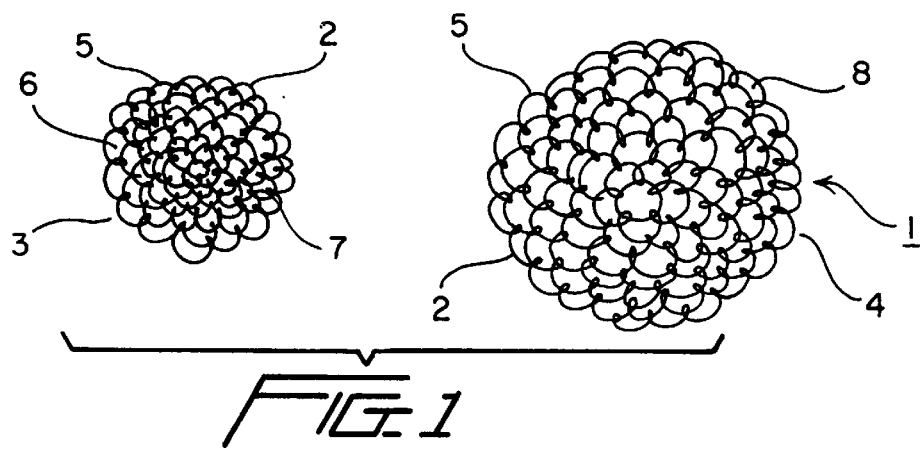
FIG. 1 is a top view of two electromagnetic shielding apparatuses of the instant invention demonstrating different coiling pitches for beanie-configured embodiments.

The present invention relates to an electromagnetic shielding apparatus 1 for the head. As shown in FIG. 1, the electromagnetic shielding apparatus may comprise a beanie configuration 3, 4 including a basic head covering 2 which is fabricated from a web of coiled and interlocking metal wire 5. Because of its availability, cost and conductivity, copper wire is an ideal material, although any other highly conductive material, including for example, bronze or brass, also would be acceptable. A preferred material is copper wire having a guage size of about 1.0 mm to about 1.0 cm. Importantly, the selected material should not be readily magnetizable in order to avoid inadvertent EMF exposure arising from the shield itself. The beanie configurations 3 and 4 differ in size in order to accommodate different heads but may also differ in construction. For example, the small beanie 3 is made of a heavier gauge copper wire 5 than is the large beanie 4. Moreover, the spaces 6 between the interlocking coils 7 of the smaller beanie 3 are larger that the spaces 8 of the larger beanie 4. Ideally, the pitch of the wire coils should be selected to produce spaces averaging from about 1.0 mm to about 20.0 mm across. Alternatively, the beanies may be fabricated from a metal mesh material. The resulting beanie allows for free air permeability therethrough and is supple enough to conform to the shape of a wearer's head. As configured, the beanie configurations 3, 4 of the electromagnetic shielding apparatus of the instant invention may be worn by themselves or may be worn discretely beneath a yarmulke or similar head gear.

Figure 2:
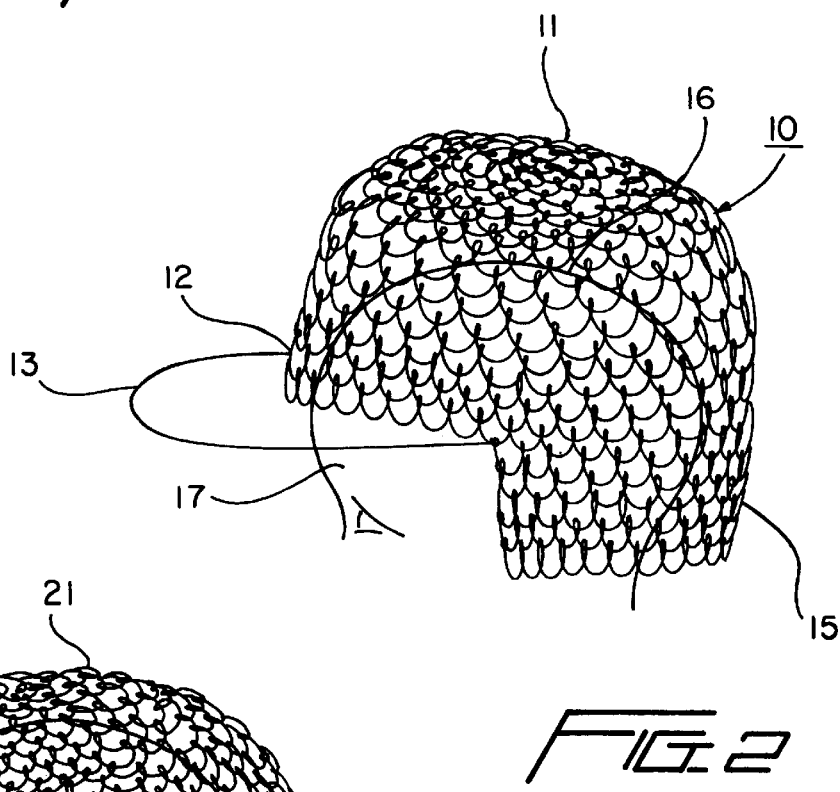
FIG. 2 is an environmental side view of another embodiment of the electromagnetic shielding apparatus of the instant invention suitable for insertion into a cap.

A first alternative embodiment 10 is shown in FIG. 2. As with the preceding embodiment, the electromagnetic shielding apparatus is fabricated as a one-piece structure having a basic head-covering portion 11, a forehead-covering portion 12 and a bill portion 13. The electromagnetic shielding apparatus thus configured may be incorporated into a cap 15, such as a baseball cap. The shielding available to the wearer is extended to include not only the top of the head 16 but also the forehead 17, generally covering the entire brain. It is to be understood that although the electromagnetic shielding apparatus is shown in conjunction with a baseball cap, hats having different configurations such as fedoras or cowboy hats are contemplated to be within the scope of the present invention, the electromagnetic shielding apparatus requiring corresponding configurational changes to conform to differing hat types. Use of lightweight materials such as the interlocking coils or mesh used in the instant invention facilitates the ready modeling of these different configurations.

Figure 3:
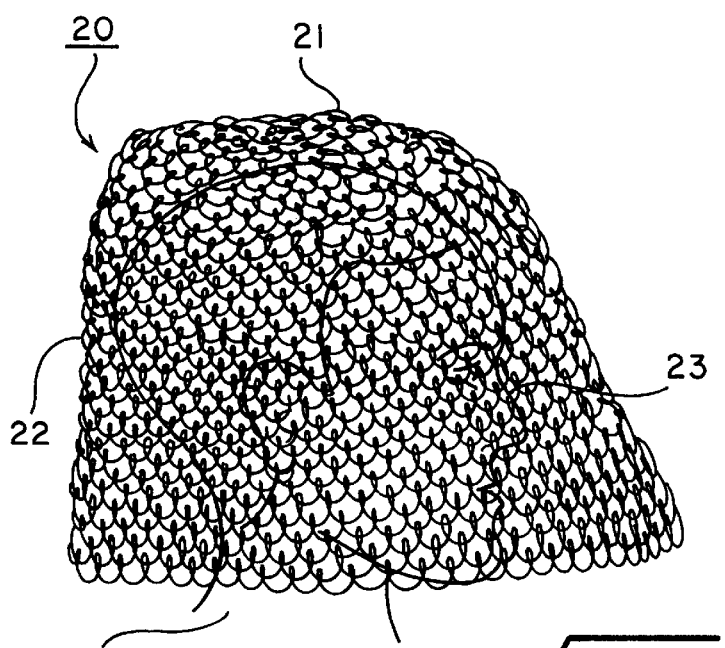
FIG. 3 is an environmental side view of another embodiment of the electromagnetic shielding apparatus of the instant invention.

A second alternative embodiment 20 shown in FIG. 3 comprises a one-piece structure including a basic head-covering portion 21 as well as a depending skirt portion 22 and may be worn to cover the entire face 23 and neck 24 of a user so that the entire head is protected from undesired EMF radiation.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. An electromagnetic shielding apparatus for protecting a wearer's head, in the form of a basic head covering composed solely of a metal wire of helically interlocking metal wire coils having a gauge size of from about 1.0 mm to about 1.0 cm, said metal wire being formed into a web of said helically interlocking metal coils, each of said helically interlocking metal wire coils delimiting a space permeable to air, said space delimited by each of said plurality of interlocking metal wire coils being from about 1.0 mm to about 20.0 mm across.

2. The electromagnetic shielding apparatus of claim 1, wherein said metal wire is copper wire.

3. The electromagnetic shielding apparatus of claim 1, wherein said metal wire is brass wire.

4. The electromagnetic shielding apparatus of claim 1, wherein said metal wire is bronze wire.

5. The electromagnetic shielding apparatus of claim 1, wherein said metal wire is composed of a conductive, non-magnetizable metal.

6. An electromagnetic shielding apparatus for protecting a wearer's head, comprising a one-piece structure including a basic head-covering portion, a forehead-covering portion and a bill portion, said one-piece structure being formed from a web consisting of a plurality of helically interlocking metal wire coils having a size of from about 1.0 mm to about 1.0 cm, each of said plurality of helically interlocking metal wire coils delimiting a space permeable to air, said space delimited by each of said plurality of interlocking metal wire coils being from about 1.0 mm to about 20.0 mm across.

7. The electromagnetic shielding apparatus of claim 6, wherein said metal wire is copper wire.

8. The electromagnetic shielding apparatus of claim 6, wherein said metal wire is brass wire.

9. The electromagnetic shielding apparatus of claim 6, wherein said metal wire is bronze wire.

10. The electromagnetic shielding apparatus of claim 6, wherein said metal wire is composed of a conductive, non-magnetizable metal.

11. An electromagnetic shielding apparatus for protecting a wearer's head, comprising a one-piece structure including a basic head covering portion and a skirt portion depending therefrom, said one-piece structure being formed from a web consisting of a plurality of each of said plurality of helically interlocking metal wire coils delimiting a space permeable to air, said space delimited by each of said plurality of interlocking metal wire coils being from about 1.0 mm in to about 20.0 mm across.

12. The electromagnetic shielding apparatus of claim 11, wherein said metal wire is copper wire.

13. The electromagnetic shielding apparatus of claim 1 1, wherein said metal wire is brass wire.

14. The electromagnetic shielding apparatus of claim 11, wherein said metal wire is bronze wire.

15. The electromagnetic shielding apparatus of claim 11, wherein said metal wire is composed of a conductive, non-magnetizable metal.

* * * * *